United States Patent [19]
Saito et al.

[11] Patent Number: 6,027,908
[45] Date of Patent: Feb. 22, 2000

[54] METHOD FOR DIFFERENTIATING VAGINAL SECRETORY FLUID OR CERVICAL MUCUS OF PREGNANT WOMAN SUFFERING FROM THREATENED PREMATURE DELIVERY

[75] Inventors: Shigeru Saito, Habikino; Motohiko Ichijo, Nara; Makiko Maeda; Masayuki Nozawa, both of Tokyo, all of Japan

[73] Assignee: Daiichi Pure Chemicals Co., Ltd., Tokyo, Japan

[21] Appl. No.: 08/718,473

[22] PCT Filed: Apr. 7, 1995

[86] PCT No.: PCT/JP95/00692

§ 371 Date: Oct. 7, 1996

§ 102(e) Date: Oct. 7, 1996

[87] PCT Pub. No.: WO95/27900

PCT Pub. Date: Oct. 19, 1995

[30] Foreign Application Priority Data

Apr. 8, 1994 [JP] Japan ..................................... 6-070659

[51] Int. Cl.$^7$ ................................................. G01N 33/53
[52] U.S. Cl. ......................... 435/7.92; 435/7.1; 435/7.92; 436/501; 436/518; 436/531; 436/811; 436/815
[58] Field of Search .................................. 435/7.1, 7.92; 436/501, 518, 531, 811, 815

[56] References Cited

U.S. PATENT DOCUMENTS

| | | | |
|---|---|---|---|
| 4,919,889 | 4/1990 | Jones et al. | 422/40 |
| 5,516,702 | 5/1996 | Senyei et al. | 436/510 |

FOREIGN PATENT DOCUMENTS

WO 93/09438  5/1993  WIPO.

OTHER PUBLICATIONS

Laham et al., "Interleukin 8 concentrations in amniotic fluid and peripheral venous plasma during human pregnancy and parturition," Acta Endocrinologica, vol. 129, pp. 220–224 (1993).

Shimoya et al., "Human Placenta Constitutively Produces Interleukin–8 during Pregnancy and Enhances Its Production in Intrauterine Infection," Biology of Reproduction, vol. 47, pp. 220–226 (1992).

Solberg E. H. in : Textbook of Clinical Chemistry, (ed) N. W. Tietz, W.B. Saunders Company, Philadelphia. 1986. Chapter 2b, pp. 356–363.

ACTA Obstetrica et Gynaecologica Japonica, vol. 46, Feb. 1994, "The 46th Lecture Meeting of the Japanese Obstetrics and Gynecology Society", pp. 1–9.

Steinborn et al., "Cytokines in the diagnosis of amniotic infection syndrome," *Zeitschrift fuer Gevurtshilfe und Perinatologie*, vol. 198, No. 1, pp. 1–5, (Jan–Feb. 1994).

Morrison et al., "Oncofetal Fibronectin in Patients with False Labor as a Predictor of Preterm Delivery," American Journal of Obstetrics and Gynecology, vol. 168, No. 2, pp. 538–542 (1993).

Saito et al., "Elevation of Amniotic Fluid Interleukin 6 IL–6 IL–8 and Granulocyte Colony Stimulating Factor G–CSF in Term and Preterm Parturition," *Cytokine*, vol. 5, No. 1, pp. 81–88 (1993).

*Primary Examiner*—James C. Housel
*Assistant Examiner*—Quang N. Phan
*Attorney, Agent, or Firm*—Oblon, Spivak, McClelland, Maier & Neustadt, P.C.

[57] ABSTRACT

Described is a method for differentiating the vaginal secretory fluid or cervical mucus of a pregnant woman suffering from threatened premature delivery, which comprises measuring an amount of Interleukin-8 in the vaginal secretory fluid or cervical mucus. The above method makes it possible to differentiate the vaginal secretory fluid or the like of the pregnant woman suffering from threatened premature delivery with good sensitivity and therefore is useful for the detection, treatment or the like of premature delivery.

3 Claims, 3 Drawing Sheets

METHOD FOR DIFFERENTIATING VAGINAL SECRETORY FLUID OR CERVICAL MUCUS OF PREGNANT WOMAN SUFFERING FROM THREATENED PREMATURE DELIVERY

TECHNICAL FIELD

The present invention relates to a method for differentiating the vaginal secretory fluid or cervical mucus of a pregnant woman suffering from threatened premature delivery, which method is useful for the detection of premature delivery.

BACKGROUND ART

Premature delivery is one of the abnormalities which occur accompanied with pregnancy. It is caused by various reasons but ascendens infection, intrauterine infection and abruption of placenta are considered as main reasons.

In the case where the premature delivery occurs because of an infectious disease or chorionic amnionitis, the concentration of C-reactive protein (CRP) and the leukocyte count both in the blood of the mother's body show an increase so that premature delivery is checked by measuring these values.

It is however difficult to say that the CRP concentration and the leukocyte count are specific to the premature delivery, because they are the values available from the blood and show an increase even by the factors other than the premature delivery. In addition, the CRP is accompanied with the problem that it can be detected only in a trace amount in the blood so the sensitivity of the measurement is low. Thus, it is difficult to make diagnosis as premature delivery at early stages of pregnancy by measuring the CRP concentration or the leukocyte count in the blood.

On the contrary, a method of making diagnosis as abortion or premature delivery by measuring Interleukin-6 (IL-6) in the blood has recently been reported (Japanese Patent Application No. 209882/1993). This method however uses the blood from the mother's body as a specimen and therefore is not fully satisfactory from the viewpoints of inferiority both in sensitivity and specificity.

An object of the present invention is therefore to search a substance which will be an indication of premature delivery and to establish a method for differentiating it.

With the forgoing in view, the present inventors have conducted an extensive investigation. As a result, it has been found that an increase in Interleukin-8 (IL-8) in the vaginal secretory fluid or cervical mucus is specific to a pregnant woman suffering from the threatened premature delivery and the vaginal secretory fluid or cervical mucus of the pregnant woman suffering from the threatened premature delivery can be differentiated by measuring the IL-8 amount, leading to the completion of the invention.

DISCLOSURE OF THE INVENTION

The present invention relates to a method for differentiating the vaginal secretory fluid or cervical mucus of a pregnant woman suffering from threatened premature delivery, which comprises measuring an amount of Interleukin-8 in the vaginal secretory fluid or cervical mucus.

BEST MODE FOR CARRYING OUT THE INVENTION

Figure 1:
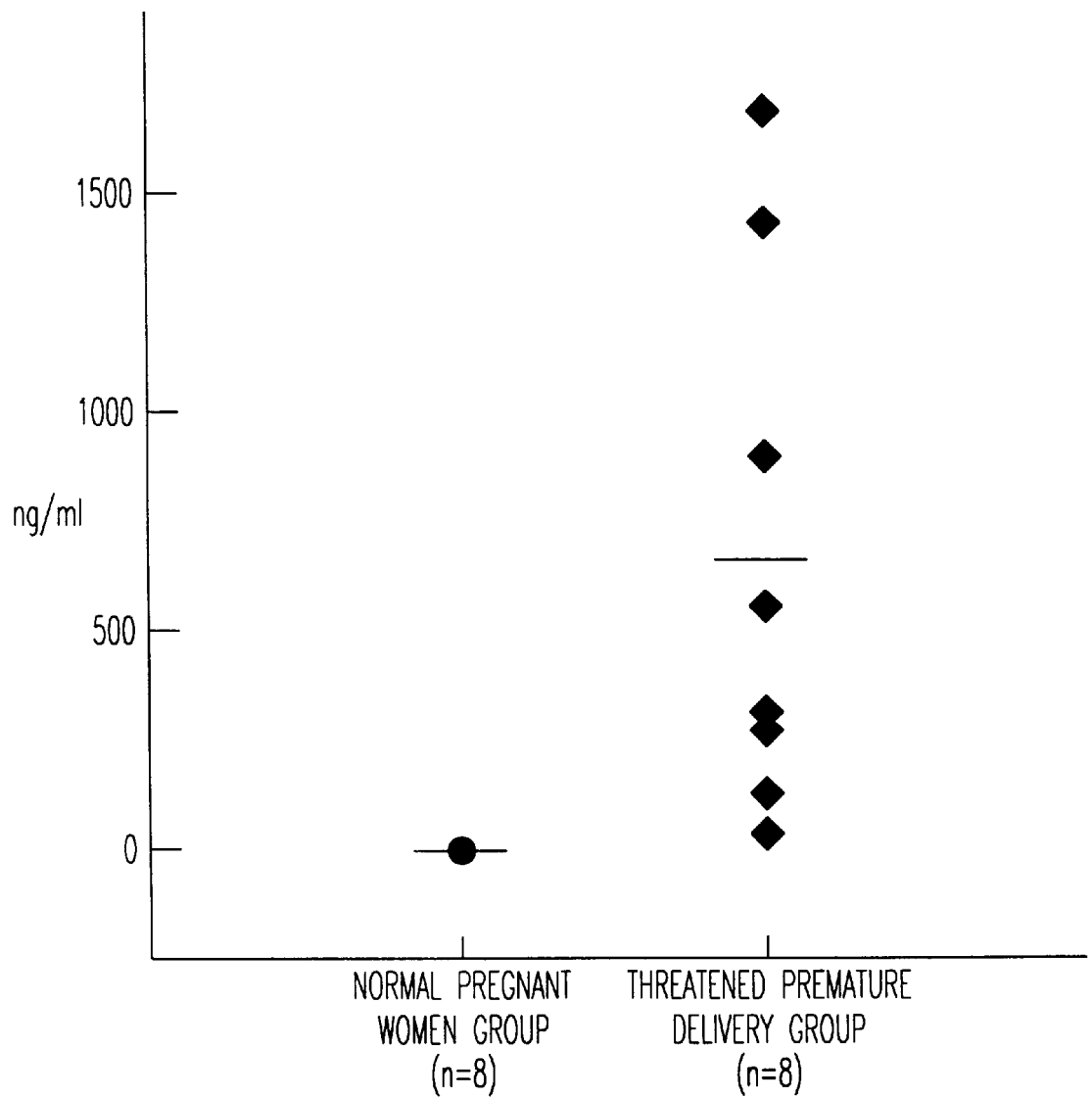
FIG. 1 illustrates a comparison in the IL-8 concentration in the vaginal secretory fluid between the normal pregnant women group (left) and the threatened premature delivery group (right).

As the specimen usable in the present invention, either a vaginal secretory fluid or cervical mucus can be used. No particular limitation is imposed on the sampling method of it insofar as the sampling can be conducted without giving a damage to the vagina or the uterine cervix. Examples include the method in which sampling is conducted by attaching a tube such as silicone tube or a needle to the end of a syringe and then inserting it in the vagina; a method in which sampling is conducted by inserting the syringe itself into the vagina; a method in which an absorber, such as an applicator, is inserted into the posterior vaginal formix and then, is allowed to absorb therein cervical mucus. Of these, the method employing an applicator is convenient and is therefore preferred, with the use of a dacron applicator as the applicator being more preferred because it brings about an improvement in an extracting efficiency. When the specimen is sampled using the applicator, the impurities in the vagina are first removed by a tampon and then the sampling is conducted while ensuring the sampling by a colposcope.

The specimen so sampled can be provided as is for the measurement. It is however desired to use it after dilution or extraction, because the undiluted vaginal secretory fluid or cervical mucus has a markedly high viscosity and is often gelated or clotted. It is preferred to use a buffer having a pH of from 6 to 8 for dilution or extraction. Examples of the buffer include phosphate buffer, tris buffer and Good's buffer. It is more preferred that the pH of the buffer falls within a range of from 7.2 to 7.8.

With a view to conducting dilution or extraction of the specimen by using the above-exemplified buffer, when the specimen is sampled using, for example, a syringe, it is preferred to extract IL-8 of the specimen, which is in the gel or clotted form, in the buffer by crushing the specimen as if cutting it and mixing the crushed substance with the buffer. In this case, it is preferred to use the buffer in an amount of at least 5 times as much as that of the specimen to conduct sufficient extraction.

When the specimen is sampled using an applicator, it is preferred to extract the specimen in a buffer by dipping the applicator, which has absorbed therein the specimen, in the buffer and then stirring the buffer with this applicator.

Any known method can be used for the measurement of the IL-8 amount in the vaginal secretory fluid or cervical mucus insofar as it is a method which can measure the cytokine amount, for example, bioassay method or immunoassay method. It is particularly preferred to employ an immunoassay method.

For example, the IL-8 in the specimen may be measured by the ELISA method in a manner known per se in the art. For example, a 96-well microtiter plate sensitized with the first antibody, that is a monoclonal or polyclonal antibody specific to IL-8, is used as a solid phase and it is reacted with the specimen, whereby the antibody on the solid phase is combined with IL-8 in the specimen. The unreacted protein is removed by a washing operation, followed by the reaction with the second antibody, that is, an enzyme-labeled monoclonal or polyclonal antibody specific to IL-8, whereby a sandwich is formed by the antigen-antibody reaction via IL-8. After the excess second antibody is removed by washing, a solution of the substrate for the labeled enzyme of the second antibody is added for color development. The enzyme reaction is then terminated by a terminating solution. The absorbance is then measured by an absorptiometer, and the IL-8 concentration in the sample may be obtained by conversion from a calibration curve of a standard product.

Alternatively, a commercially-available sandwich ELISA kit for the measurement of IL-8 concentration can be used.

Based on the IL-8 amount measured in this way, the vaginal secretory fluid or cervical mucus of a pregnant woman suffering from the threatened premature delivery can be differentiated. Described specifically, the vaginal secretory fluid showing a value higher than the IL-8 amount of the normal pregnant woman is regarded as that of a pregnant woman suffering from the threatened premature delivery.

Thus, it is possible to differentiate the normal pregnant woman and the pregnant woman suffering from the threatened premature delivery by measuring the IL-8 amount in their vaginal secretory fluids or cervical mucus.

EXAMPLES

The present invention will hereinafter be described in detail by the following examples. It should however be borne in mind that the present invention is not limited to or by the examples.

Example 1

Concerning eight normal pregnant women who were different in each gestational age and eight pregnant women who had been diagnosed as threatened premature delivery, the IL-8 amount in the vaginal secretory fluid, the CRP concentration in the serum and the leukocyte count in the blood were measured as described below, respectively. These results are shown in Table 1, Table 2 and FIG. 1.

Sampling Method of Specimen

A dacron applicator was inserted in the posterior vaginal formix of each of the pregnant women. The applicator was turned round for about ten minutes to have the vaginal secretory fluid absorbed in it, followed by dipping in 1 µl of an extracting solution (which comprises 50 mM of 2-amino-2-hydroxymethyl-1,3-propanediol, 1% BSA, 0.89% of sodium chloride, 0.2% of disodium ethylenediaminetetraacetate, 1 µl/ml of aprotinin, 1 µl/ml of dimethylsulfoxide, 0.17 mg/ml of phenylmethylsulfonyl fluoride, 1 µl/ml of polyoxyethylenoctyl phenyl ether and 0.5 mg/ml of sodium azide; pH 7.5). The vaginal secretory fluid absorbed in the dacron applicator was extracted by stirring the extracting solution with the dacron applicator. The vaginal secretory fluid so extracted was used as a sample. Incidentally, the sample was used after dilution with the extracting solution as needed.

Measuring Method of IL-8

The IL-8 in the vaginal secretory fluid was measured, as will be described subsequently, in accordance with the measuring method of Quantikine of R & D. Described specifically, in each of the wells of the microtiter plate sensitized with a mouse anti-IL-8 monoclonal antibody, a 100 µl portion of an assay diluent was poured, followed by the addition of a 100 µl portion of the sample. The resulting mixture was then allowed to stand at room temperature for 2 hours to cause reaction, followed by washing of the well three times each with a 400 µl portion of a washing liquid. The washing liquid was thereafter removed. To each well, a 200 µl portion of a horseradish peroxidase-labeled (HRP) anti-IL-8 polyclonal antibody solution was added, which was allowed to stand at room temperature for 2 hours. After washing three times each with a 400 µl portion of the washing liquid, a 200 µl portion of a chromogenic solution containing tetramethyl bentidine as a substrate was added to each well, which was allowed to stand at room temperature for 20 minutes. To each well, a 50 µl portion of 2N sulfuric acid was added as a terminating solution, whereby the enzyme reaction was terminated. The wavelength of the microtiter plate reader was set at two wavelengths, that is, 450 nm and 550 nm, and an absorbance was measured. The IL-8 concentration in the sample was obtained from the calibration curve of the standard product by conversion.

The CRP concentration, on the other hand, was measured by a commercially available kit (product of IATRON LABORATORIES, INC., latex coagulation method) by using the serum of the pregnant woman as a sample. The leukocyte count was measured by an automatic blood cell counter of Sysmecks Corporation by using the blood of the pregnant woman.

TABLE 1

IL-8 Concentration in vaginal secretory fluid of normal pregnant women group

| Patient No. | Gestational age | IL-8 ng/ml |
| --- | --- | --- |
| 1 | 6W | 3.61 |
| 2 | 14W | 4.31 |
| 3 | 20W | 2.52 |
| 4 | 21W | 8.34 |
| 5 | 25W | 1.50 |
| 6 | 27W | 3.32 |
| 7 | 29W | 2.67 |
| 8 | 35W | 12.08 |

TABLE 2

IL-8 Concentration in vaginal secretory fluid, CRP concentration in serum and leukocyte count in blood, of threatened premature delivery group

| Patient No. | Gestational age | In vaginal secretory liquid IL-8 ng/ml | In serum CRP mg/dl | In blood Leukocyte count /mm$^3$ |
| --- | --- | --- | --- | --- |
| 1 | 25W + 4d | 292 | 0.30 | 9900 |
| 2 | 24W + 3d | 128 | 0.00 | 10500 |
| 3 | 32W + 3d | 1680 | 16.40 | 12000 |
| 4 | 25W + 2d | 554 | 0.50 | 6800 |
| 5 | 30W + 4d | 890 | 0.30 | 7800 |
| 6 | 28W + 2d | 323 | 0.30 | 12700 |
| 7 | 31W + 5d | 41.5 | 0.00 | 5100 |
| 8 | 26W + 1d | 1430 | 2.80 | 16000 |

The concentration of IL-8 in the vaginal secretory fluid was 1.5–12.1 ng/ml in the case of the normal pregnant women, while that was 41.5–1680 ng/ml in the case of the group of threatened premature delivery. According to the Mann-Whiteney's test, the IL-8 concentration of the latter group showed a significantly high value ($p<0.001$). From these results, it has been found that the measurement of the amount of IL-8 in the vaginal secretory fluid makes it possible to differentiate the vaginal secretory fluid of a pregnant woman who suffers from threatened premature delivery, thereby detecting the premature delivery.

On the contrary, there exist six samples, among eight samples of the threatened premature delivery group, which did not show an abnormal value in the CRP concentration (0.8 mg/dl or higher) in the serum so that premature delivery could not be detected effectively from the CRP concentration in the blood.

Concerning the leukocyte count in the blood, three examples, among eight examples of the threatened premature delivery group, showed a normal value (4,000–8,000/mm$^3$) so that it was not impossible to detect all the threatened premature delivery cases from the test of the leukocyte count.

Example 2

Figure 2:
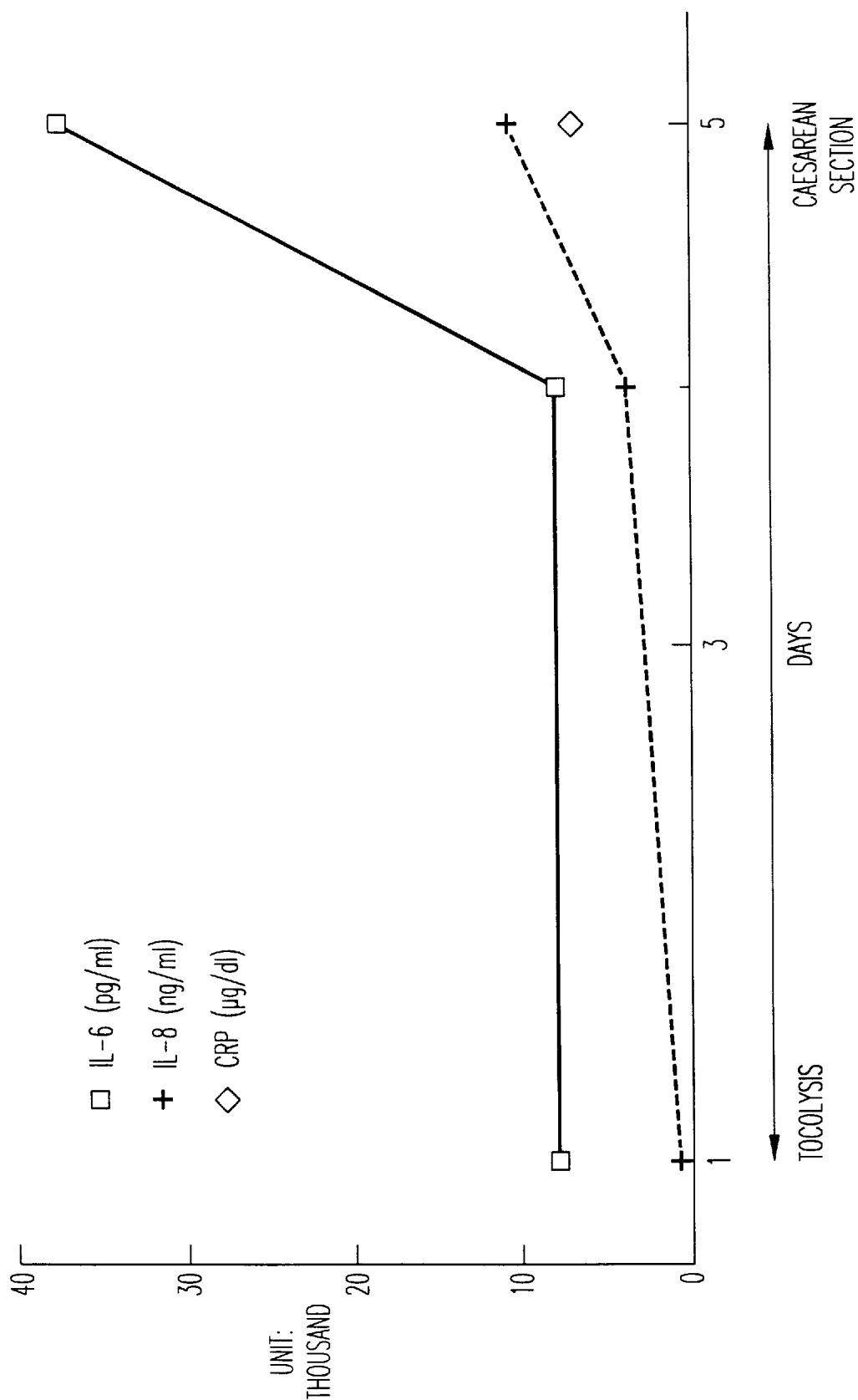
FIG. 2 illustrates fluctuations in the IL-6 and IL-8 concentrations in the vaginal secretory fluid and the CRP concentration in the serum, each obtained from pregnant women who were diagnosed as threatened premature delivery, received treatment but lead to premature delivery.

FIG. 2 illustrates a case which was diagnosed as threatened premature delivery at the gestational age of 20 weeks, received a tocolysis treatment, but resulted in premature delivery on the fifth day after the treatment was started. The IL-6 and IL-8 concentrations in the vaginal secretory fluid and the CRP concentration in the serum are plotted along the ordinate, while the days after the first examination are plotted along the abscissa.

The IL-6 and IL-8 concentrations in the vaginal secretory fluid of a pregnant woman were measured by sampling and extracting the specimen in a similar manner to Example 1. The IL-6 and IL-8 concentrations were measured using an ELISA kit for IL-6 measurement (product of R&D) and an ELISA kit for IL-8 measurement (product of R&D), respectively.

Consequently, both the IL-6 and IL-8 concentrations continued increasing, resulting in the premature delivery. The IL-8 concentration is, however, by about $10^3$ higher than the IL-6 concentration so that the premature delivery can be detected with better sensitivity by using the IL-8 concentration. The CRP concentration in the serum, which had been used conventionally for the detection of the premature delivery, only showed an abnormal value just before the premature delivery.

Example 3

Figure 3:
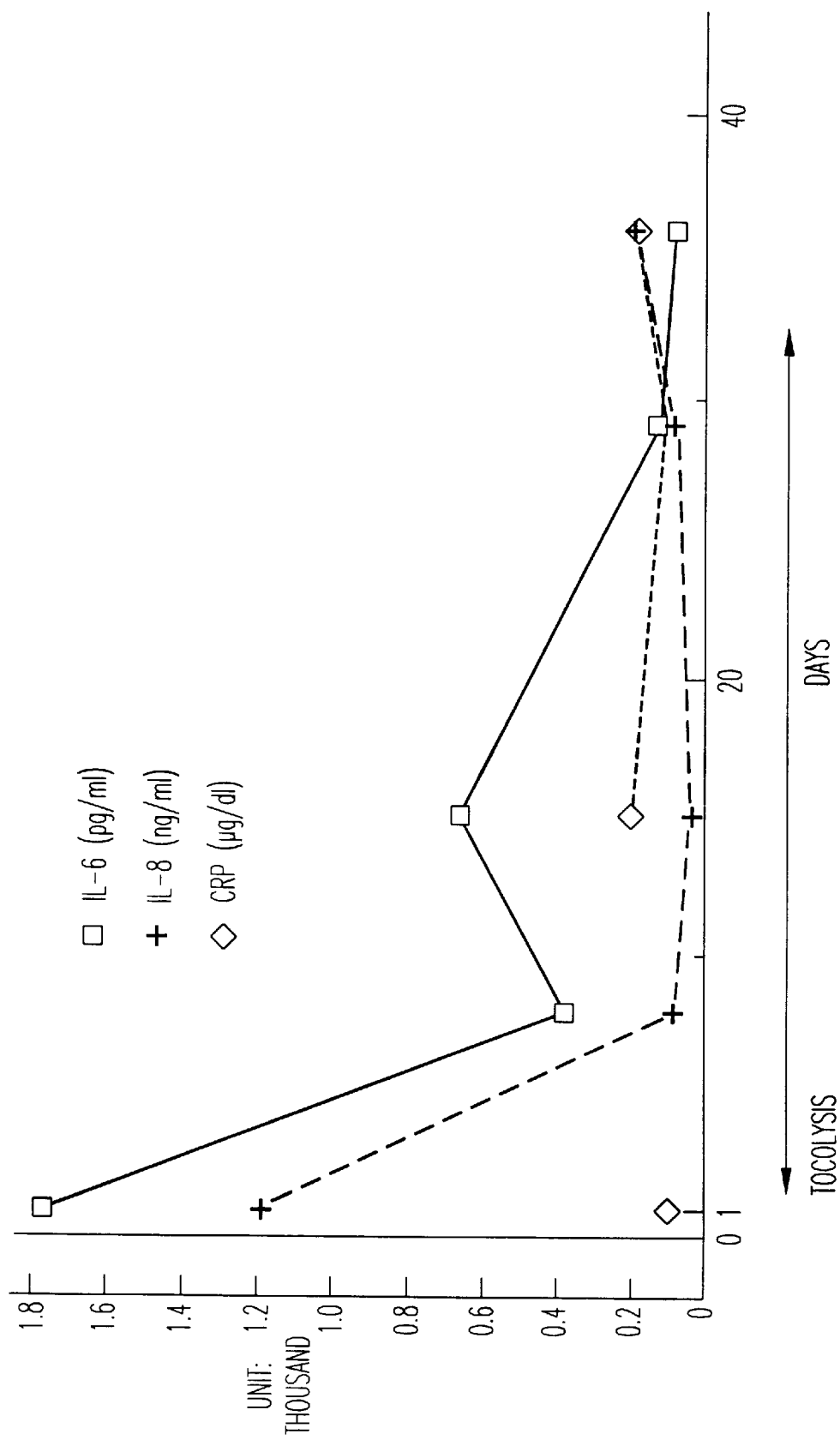
FIG. 3 illustrates fluctuations in the IL-6 and IL-8 concentrations in the vaginal secretory fluid and the CRP concentration in the serum, each obtained from pregnant women who were diagnosed as threatened premature delivery but as a result of treatment, recovered and lead to full-term normal delivery.

FIG. 3 illustrates a case which was diagnosed as the premature delivery at the gestational age of 30 weeks, received a tocolysis treatment and resulted in the full term delivery. The IL-6 and IL-8 concentrations in the vaginal secretory fluid and the CRP concentration in the serum are plotted along the ordinate, while the days after the first examination are plotted along the abscissa. The IL-6 and IL-8 concentrations in the vaginal secretory fluid of a pregnant woman were measured by sampling and extracting the specimen in a similar manner to Example 1.

The more stable the symptom became, the lowering tendency the IL-6 and IL-8 concentrations showed. For monitoring the judgment of the effects brought about by the treatment, the IL-8 concentration is superior because it is by about $10^3$ higher than the IL-6 concentration so that the premature delivery can be detected with better sensitivity by using the IL-8 concentration.

Example 4

Fluctuations in the IL-8 concentrations in the serum and in the vaginal secretory fluid of the threatened premature delivery group were measured in a similar manner to Example 1. The results are shown in Table 3.

TABLE 3

Comparison between IL-8 concentration in vaginal secretory fluid and that in serum, both of threatened premature delivery group

| Patient No. | Gestational age | In vaginal secretory liquid IL-8 ng/ml | In serum IL-8 ng/ml |
| --- | --- | --- | --- |
| 1 | 27W + 3 | 154 | <0.03 |
| 2 | 32W | 73.80 | <0.03 |
| 3 | 33W + 1 | 737 | <0.03 |
| 4 | 37W + 1 | 89.50 | <0.03 |

The amount of IL-8 in the serum is as small as the lowest limit of the measuring range, while the IL-8 exists in the vaginal secretory fluid in an amount sufficient for the measurement. Accordingly, the use of the vaginal secretory fluid as a sample, said fluid being close to the object of the treatment, makes it possible to differentiate the vaginal secretory fluid of the pregnant woman suffering from threatened premature delivery even in a small amount and also to detect the premature delivery with better sensitivity than the use of the serum, plasma or blood.

Example 5

The IL-8, CRP in the serum and the leukocyte count in the blood were measured in a similar manner to Example 1 concerning the case which was diagnosed as threatened premature delivery at the gestational age of 30 weeks, received a tocolysis treatment but resulted in the premature delivery through caesarean section on the 20th day. The results are shown in Table 4.

TABLE 4

IL-6 and IL-8 Concentrations in vaginal secretory fluid (premature delivery), CRP concentration in serum and leukocyte count in blood, of a case beyond remedy

| Days after first examination | In vaginal secretory liquid IL-8 ng/ml | In serum CRP mg/dl | In blood Leukocyte count /mm$^3$ |
| --- | --- | --- | --- |
| The first examination day | 890 | 0.3 | 7800 |
| 10th day | 378 | 0.5 | 8500 |
| 20th day | 4120 | 3.7 | 14200 |

From the results of the first examination day, it has been found that the IL-8 in the vaginal secretory fluid showed a high concentration which could be judged as abnormal, but the CRP concentration in the serum and the leukocyte in the blood each fell in its normal range. The IL-8 concentration continued to be high after that, leading to the premature delivery, while, the leukocyte count showed an abnormal value on the 10th day after the first examination and the CRP concentration became abnormal just before the premature delivery. Thus, the measurement of the IL-8 concentration in the vaginal secretory fluid makes it possible to differentiate the vaginal secretory fluid of a pregnant woman suffering from threatened premature delivery, and also to detect the premature delivery at earlier stages of the pregnancy compared with the measurement in the CRP concentration in the serum or the leukocyte count in the blood.

Example 6

Measured were the IL-6 and IL-8 amounts in the vaginal secretory fluid of 35 normal pregnant women who were different in each gestational age and 38 pregnant women who were diagnosed as threatened premature delivery. The sampling of the specimen and measurement of the IL-6 and IL-8 amounts were conducted in a similar manner to Example 1. The results are shown in Tables and 5 and 6.

TABLE 5

| Group of normal pregnant women | | In vaginal secretory fluid | |
|---|---|---|---|
| Specimen No. | Gestational age | IL-6 ng/ml | IL-8 ng/ml |
| 1 | 6W | 0.108 | 13.5 |
| 2 | 6W | 0.807 | 8.0 |
| 3 | 6W | 0.132 | 3.6 |
| 4 | 6W + 3d | 1.475 | 14.4 |
| 5 | 10W | 0.277 | 43.1 |
| 6 | 14W | 0.000 | 4.3 |
| 7 | 18W | 0.188 | 10.4 |
| 8 | 18W | 0.142 | 104.2 |
| 9 | 19W | 0.339 | 4.3 |
| 10 | 20W | 0.000 | 2.5 |
| 11 | 21W | 0.130 | 44.2 |
| 12 | 21W | 0.077 | 41.2 |
| 13 | 21W | 0.000 | 8.3 |
| 14 | 22W | 0.177 | 44.3 |
| 15 | 23W | 0.111 | 59.8 |
| 16 | 24W | 0.106 | 84.6 |
| 17 | 25W | 0.000 | 1.5 |
| 18 | 26W | 0.138 | 59.3 |
| 19 | 27W | 0.162 | 3.3 |
| 20 | 28W | 0.082 | 50.9 |
| 21 | 28W | 0.076 | 22.9 |
| 22 | 28W | 0.295 | 42.4 |
| 23 | 29W | 0.000 | 2.7 |
| 24 | 31W | 0.000 | 44.6 |
| 25 | 32W | 0.000 | 26.9 |
| 26 | 32W | 0.130 | 87.0 |
| 27 | 32W | 0.121 | 21.5 |
| 28 | 34W + 6d | 0.237 | 19.8 |
| 29 | 35W | 0.096 | 12.1 |
| 30 | 35W + 1d | 1.667 | 50.9 |
| 31 | 36W | 0.134 | 40.6 |
| 32 | 36W | 0.090 | 41.8 |
| 33 | 36W | 0.211 | 68.7 |
| 34 | 40W | 0.227 | 12.3 |
| 35 | 40W | 0.888 | 23.5 |
| Average | | 0.246 | 32.10 |
| Standard deviation | | 0.383 | 27.02 |
| Average + 2 standard deviation | | 1.012 | 86.14 |

TABLE 6

| Group of threatened premature delivery Specimen No. | In vaginal secretory fluid | |
|---|---|---|
| | IL-6 ng/ml | IL-8 ng/ml |
| 1 | 1.12 | 1,090 |
| 2 | 3.95 | 467 |
| 3 | 3.36 | 888 |
| 4 | 0.95 | 292 |
| 5 | 1.61 | 128 |
| 6 | 0.00 | 410 |
| 7 | 0.10 | 82.3 |
| 8 | 0.22 | 227 |
| 9 | 4.98 | 180 |
| 10 | 0.14 | 332 |
| 11 | 0.00 | 108 |
| 12 | 0.81 | 808 |
| 13 | 0.33 | 101 |
| 14 | 0.00 | 96.7 |
| 15 | 0.21 | 98.5 |
| 16 | 0.08 | 423 |
| 17 | 0.23 | 137 |
| 18 | 0.00 | 535 |
| 19 | 1.91 | 1,120 |
| 20 | 1.23 | 316 |
| 21 | 0.70 | 282 |
| 22 | 1.56 | 295 |
| 23 | 1.35 | 43.6 |
| 24 | 3.07 | 449 |
| 25 | 0.32 | 2,440 |
| 26 | 1.14 | 625 |
| 27 | 0.34 | 126 |
| 28 | 10.60 | 204 |
| 29 | 1.77 | 1,190 |
| 30 | 5.73 | 1,680 |
| 31 | 7.83 | 554 |
| 32 | 0.42 | 890 |
| 33 | 0.74 | 323 |
| 34 | 1.61 | 42 |
| 35 | 13.00 | 1,430 |
| 36 | 2.89 | 1,064 |
| 37 | 0.39 | 110 |
| 38 | 0.00 | 144 |

The criterion on concentration (cut-off value) of threatened premature delivery was designated as the average value the IL-6 or IL-8 concentration in the vaginal secretory fluid in a normal pregnant woman+2 standard deviation, and the sensitivity and specificity of the IL-6 and IL-8 to threatened premature delivery were calculated in accordance with the following formulas, respectively. The results are shown in Table 7.

$$\text{Sensitivity (\%)} = \frac{\text{The number of the specimens having a concentration of at least the cut-off value (the number of positive substances), among the threatened premature delivery group}}{\text{The number of the specimens of pregnant women suffering from threatened premature delivery}} \times 100$$

$$\text{Specificity (\%)} = \frac{\text{The number of the specimens having a concentration of at most the cut-off value (the number of positive substances), among the normal pregnant women group}}{\text{The number of the specimens of normal pregnant women}} \times 100$$

TABLE 7

| | IL-6 | IL-8 |
|---|---|---|
| Cut-off concentration | 1.012 ng/ml | 86.14 ng/ml |
| Sensitivity | 47% | 92% |
| Specificity | 94% | 94% |

As is apparent from the results in Table 7, compared with IL-8showed both high sensitivity and high specificity, which are the requirements for a detection reagent, so that it is useful for the detection of threatened premature delivery.

CAPABILITY OF EXPLOITATION IN INDUSTRY

According to the present invention, the vaginal secretory fluid or cervical mucus of the pregnant woman suffering from threatened premature delivery can be differentiated with better sensitivity, so that the method according to the present invention is useful for the detection, diagnosis and treatment of premature delivery.

We claim:

1. A method of diagnosing possible premature delivery comprising measuring a level of interleukin-8 (IL-8) in vaginal secretory fluid or cervical mucus of a pregnant woman suspected of premature delivery, comparing the level with that of a normal pregnant woman, and correlating an IL-8 level of 86.14 ng/ml or more in the pregnant woman suspected of premature delivery with a possibility of premature delivery.

2. A method according to claim 1, wherein the vaginal secretory fluid or cervical mucus has been sampled by inserting a dacron applicator in the posterior vaginal formix, thereby having the vaginal secretory fluid or cervical mucus absorbed in it.

3. A method according to claim 1, wherein the vaginal secretory fluid or cervical mucus which has been sampled is diluted or extracted with a buffer having a pH of from 6 to 8 prior to measurement of, the amount of Interleukin-8.

* * * * *